United States Patent [19]

Dybas

[11] Patent Number: 4,560,677

[45] Date of Patent: Dec. 24, 1985

[54] SYNERGISTIC AVERMECTIN COMBINATION FOR TREATING PLANT PESTS

[75] Inventor: Richard A. Dybas, Bridgewater, N.J.

[73] Assignee: Merck & Co., Inc., Rahway, N.J.

[21] Appl. No.: 575,614

[22] Filed: Jan. 31, 1984

[51] Int. Cl.$^4$ .................... A61K 31/70; A61K 31/365
[52] U.S. Cl. ................................... 514/30; 71/65; 71/88; 71/DIG. 1; 536/7.1; 549/264; 514/450
[58] Field of Search ...................... 424/180; 71/65, 88; 536/7.1; 549/264; 514/30

[56] References Cited

U.S. PATENT DOCUMENTS

| | | | |
|---|---|---|---|
| 4,156,720 | 5/1979 | Fisher et al. | 536/7.1 |
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 424/180 |
| 4,206,205 | 6/1980 | Mrozik et al. | 424/180 |
| 4,310,519 | 1/1982 | Albers-Schonberg et al. | 424/181 |
| 4,333,925 | 6/1982 | Buhs et al. | 536/7.1 |

FOREIGN PATENT DOCUMENTS 964482  3/1975  Canada ................................ 536/7.1

OTHER PUBLICATIONS

Kirk et al., *Encyclopedia of Chemical Technology*, 13, pp. 515–517 (1954).
Yamamoto et al., *Jap. J. Appln. Ent. Zool.*, 25, pp. 182–190 (1981).

*Primary Examiner*—Johnnie R. Brown
*Attorney, Agent, or Firm*—David L. Rose; Michael C. Sudol, Jr.; Mario A. Monaco

[57] ABSTRACT

There is disclosed a novel combination of avermectin compounds and agricultural spray oil which has been found to be synergistic in such a manner as to allow for a drastic reduction in the amount of active ingredient which is fully effective and also a dramatic extension of the time period over which such a combination is fully effective. The synergistic combination is useful as an agricultural insecticide and miticide against a variety of insects and mites which infest a variety of plants.

7 Claims, No Drawings

SYNERGISTIC AVERMECTIN COMBINATION FOR TREATING PLANT PESTS

BACKGROUND OF THE INVENTION

The avermectins (formerly identified as C-076 compounds) are a family of macrocyclic lactones which have been found to be highly effective against a broad range of pests which infest and are an annoyance to plants and animals. The compounds are active against ectoparasites and endoparasites of domestic animals, including food and pet animals and also man. In addition, the compounds are very effective against arthroped pests which affect plants while in storage or while growing either in the aerial portion of the plant or from the soil in which they grow.

The avermectin compounds are isolated from the fermentation broth of a microorganism, *Streptomyces avermitilis*. The isolation and purification of such compounds is described in U.S. Pat. No. 4,310,519 issued Jan. 12, 1982. Several derivatives of the avermectin compounds have been prepared and such derivatives have also been found to behave synergistically in the instant combination. Specifically the 22,23-dihydro derivatives and the monosaccharide derivatives are synergized by the instant combination.

Compounds which are somewhat related to the avermectins, but which have significant chemical differences, are the milbemycins. Such compounds have been found to be active miticides and insecticides. In tests the ovicidal activity of such compounds has been seen to be enhanced by the addition of machine oil, however, such activity has been demonstrated to be significantly different from the instant synergistic activity againist the motile (active) stages of agricultural insect and mite pests. In addition, tests have shown that the milbemycin compounds, when used in the manner described herein actually have a reduced activity, that is, the combination of the milbemycin with oil has less activity than the milbemycin alone.

SUMMARY OF THE INVENTION

The instant invention is concerned with the combination of certain avermectin compounds and an agricultural spray oil such that the combination is significantly more effective at a lower dose of avermectin and over a longer period of time than either component alone. Thus it is an object of the instant invention to describe such avermectin compounds and the agriculture spray oil with which they are combined. It is a further object to describe the synergistic formulations containing the avermectin compound or compounds and such agricultural spray oils. A still further object is to describe the plants to which such formulations can be applied and the arthropod pests of such plants against which the above combination of ingredients is effective. Further objects will become apparent from a reading of the following description.

DESCRIPTION OF THE INVENTION

The avermectin compounds of the instant invention which form part of the instant synergistic combination are best described in the following structural formula:

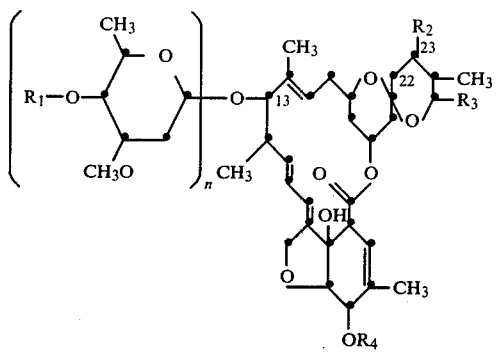

wherein
the broken line indicates either a single or a double bond at the 22,23-position.
n is 0 or 1 such that when n is 0 a hydroxy is present at the 13-position;
$R_1$ is hydrogen or

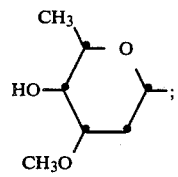

$R_2$ is hydrogen or hydroxy provided that $R_2$ is present only when the broken line indicates a single bond;
$R_3$ is sec-butyl or isopropyl; and
$R_4$ is hydrogen or methyl.

The avermectin compounds isolated from the *Streptomyces avermitilis* fermentation broth are obtained as described in the above-mentioned U.S. Pat. No. 4,310,519. Such compounds are those of the above formula wherein n is 1; $R_1$ is the sugar moiety (which is α-L-oleandrose); the broken line indicates a single or double bond; $R_2$ is hydroxy but is present only when the broken line indicates a single bond; $R_3$ is sec.-butyl or isopropyl; and $R_4$ is hydrogen or methyl. The compounds are named using a combination of letters and numbers which coordinate with the structural variations of the substituents. The following table defines the avermectin natural product compounds:

| Avermectin | $R_1/\Delta 22,23$ | $R_3$ | $R_4$ |
|---|---|---|---|
| A1a | Double bond | sec-butyl | —$CH_3$ |
| A1b | Double bond | isopropyl | —$CH_3$ |
| A2a | —OH | sec-butyl | —$CH_3$ |
| A2b | —OH | isopropyl | —$CH_3$ |
| B1a | Double bond | sec-butyl | —H |
| B1b | Double bond | isopropyl | —H |
| B2a | —OH | sec-butyl | —H |
| B2b | —OH | isopropyl | —H |

Derivatives of the above 8 avermectin compounds can be prepared to form other compounds which are effective in the instant combination. In the A1a, A1b, B1a and B1b compounds (the "1-series" of compounds) the 22,23-double bond can be selectively reduced to a single bond to form the compounds wherein $R_2$ is hydrogen. The catalyst which is selective in reducing the 22,23-double bond, while not affecting the other 4 double bonds is Wilkinsons homogeneous catalyst exemplified by triphenyl phosphine rhodium chloride. The procedures for making such 22,23-dihydro avermectin compounds and fully described in U.S. Pat. No. 4,199,569 issued Apr. 22, 1980.

In addition, the outer α-L-oleandrose group can be selectively hydrolyzed to prepare the avermectin monosaccharide compounds; those compounds wherein $R_1$ is hydrogen. Hydrolysis is most readily and most selectively effected by treating the avermectin compounds with sulfuric acid in isopropanol. The procedures for preparing such monosaccharide compounds and fully described in U.S. Pat. No. 4,206,205 issued June 3, 1980.

To prepare the compounds wherein n is 0, both oleandrosyl groups are removed by hydrolysis with 1% sulfuric acid in methanol to prepare the aglycone compound. The procedures are described in the above cited U.S. Pat. No. 4,206,205. The resulting 13-hydroxy group is removed in two steps; first by preparing the 13-chloro compound with 2-nitro benzenesulfonyl chloride and reducing the 13-chloro compound to the 13-deoxy compound with tributyl tin hydride. The procedures for such reactions are described in U.S. Pat. Nos. 4,171,314 and 4,173,571.

The agricultural spray oils which form the second component of the instant combination, may be highly refined hydrocarbon oils, specially processed to remove sulfonated residues which may be toxic to plants. Generally, oil with at least 92% unsulfonated residues is employed. The oils are narrow distillation fractions and are characterized by a narrow range of physical properties. In particular, such oils are characterized in one instance by their viscosity and one such test for viscosity is measured in seconds. One of the oils useful in the instant combination is characterized in being a narrow function yielding a viscosity test of 60 seconds. This commonly is called "60 second oil" and is also known by the tradenames of Sunspray 6N, Orchex, FMC NR 415, and the like and similar 60 second oils from Superior and Volk. This particular oil is also characterized in having a boiling point of 213° C. or 415° F. Another oil used in the instant combination is a similar oil however, having a viscosity test of 70 seconds. This is called "70 second oil" and is also known by the tradenames of Sunspray 7N, FMC NR 440, and the like and similar 70 second oils from Superior and Volk. This oil is also characterized in having a boiling point of 227° C. or 440° F.

Other typical characterizations of the instant agricultural spray oils are described in the literature. See, for example, Canadian Pat. No. 964,482.

The agricultural spray oils may also be a vegetable seed oil or a mixture of vegetable seed oils, which, as they are known in the agricultural industry, are crop seed oils produced from the particular crop from which their name is derived. Included in the vegetable oils suitable for the compositions of the present invention are cotton seed oil, rapeseed, peanut oil, sunflower oil, linseed oil, safflower oil, soybean oil, corn oil, olive oil and blends of the above oils such as cotton seed oil plus soybean oil; cotton seed oil plus peanut oil; cotton seed oil plus olive oil; corn oil plus linseed oil; corn oil plus soybean oil; as well as blends of any two or more of the above disclosed vegetable oils. In addition, the instant agricultural spray oil may be a mixture of a vegetable oil or oils and the above described hydrocarbon oils.

These oils have been used alone to combat mite infestations in plants however the cncentrations used were generally in the order of 1 to 2%. In addition, such oil formulations at the 1 to 2% concentration were used in combination with insecticides. It is known that when it is used under these conditions, the oil physically smothers the eggs, thus preventing their maturing into the motile stages of development. That is, the oils acts as an ovicide.

In the instant invention the oil may be used in combination with the avermectin compound in concentrations similar to that used in the prior art, however, in such circumstances much less of the avermectin compound need be used. The combination of the agricultural spray oil and the avermectin provides effective protection against the motile stages of the mites and insects while the use of higher concentrations of the oil provides ovicidal effects. In the synergistic combination of the instant invention the agricultural spray oil is used in concentrations of from 0.03 to 2% on a volume-to-volume basis of the final formulation. Preferably concentrations of the agricultural spray oil are used from 0.06 to 0.5%, and most preferably at about 0.25%. The lower concentrations are preferred when, because of the nature of a particular plant, or because of the sensitivity of a particular stage of growth of a plant, a spray containing higher concentrations cannot be used because of phytotoxicity.

The avermectin compounds are employed in the synergistic combination at concentrations of from 0.03 to 8 parts per million (ppm). Perferably from 0.25 to 3 ppm are employed and most preferably from 1 to 3 ppm are employed in dilute solutions for optimum field control of the mite populations.

The combination of the avermectin with the agricultural spray oil provides the unexpected benefits of being able to use less of each of the ingredients as well as providing a longer duration of action.

It is also avantageous to use less of each of the ingredients since the avermectins are very expensive and the agricultural spray oils, under certain circumstances can be phytotoxic, or at least contraindicated. The surprising observation that the instant combination has a considerably prolonged duration of action is a great benefit in that costly reapplications and reinfestations are avoided.

The avermectin and the agricultural spray oil combination is prepared using a solvent solution or emulsion of the avermectin compound or compounds, the agricultural spray oil, a surfactant and sufficient water to dilute the mixture to the desired concentration.

The surfactants which may be used to emulsify the oil and the avermectin in the aqueous formulations are any of the non-phytotoxic surfactants, which are customarily used in preparing formulations for use on agricultural crops.

The surfactants or surface active agents particularly suited for use in the compositions of the present invention are ionic or nonionic surface active compounds generally well known to the art. Surface active agents are suitable as a class for use according to the present invention. The nature of surface activations is well known and such agents generally have an olephilic portion of the molecule, usually of hydrocarbon nature, and another polar portion of the molecule, which may be provided by various functional groups such as hydroxyl, sulfate, carboxyl, carbonyl, amino, nitro, amide, ether, sulfonate, phosphate, phosphite, etc. Examples of suitable classes of surface active agents which can be employed are alkali metal salts of fatty acids, alkali metal salts of sulfonated fatty acids, fatty acid glycerides, sulfonated or sulfated fatty acid esters or amides, alkali metal sulfates, alkali metal alkyl sulfonates, alkali metal aryl sulfonates, alkali metal alkyl lauryl sulfonates, quaternary ammonium halides, alkali metal salts of alkylated naphthalene, sulfonic acid, polyethylene sorbitol esters of fatty acids, fatty acid amides of alkanol amines, condensation products of ethylene oxide and polyalkylene glycols, sorbitan esters, alkyl substituted phosphoric acids, alkali metal salts of alkyl phenol sulfonates, etc. Examples of individual surface active agents which can be employed are given for example in Kirk et al., ENCYCLOPEDIA OF CHEMICAL TECHNOLOGY, Volume 13, pages 515–517 (1954).

The ingredients are combined using formulation techniques well known to those skilled in the art.

The instant synergistic combination may be used against agricultural arthropod pests to provide effective protection from the motile stages of such mites and insects while the plant is growing or while the crops from such plants are in storage. In particular, this combination is effective against mites of the order acarina such as the two spotted spider mite (*Tetranychus urticae*), the citrus red mite (*Panonychus citri*), the citrus rust mite (*Phyllocoptruta oleivora*), and the like. Insects of the order *homoptera, coleoptera* and *lepidoptera* are likewise susceptible to this combination. In particular the black bean aphid (*Aphis fabea*), Colorado potato beetle (*Leptinotarsa decemlineata*), Mexican bean beetle (*Epilachna varivestis*); cabbage looper (*Trichoplusia ni*) and the like.

In using the compounds of this invention, the individual avermectin components may be prepared and used in that form. Alternatively, mixtures of two or more of the individual avermectin components may be used, as well as mixtures of the parent avermectin compounds, other avermectin compounds, or other active compounds not related to the avermectins and the compounds of this invention.

In the isolation of the avermectin compounds, which serve as starting materials for the instant processes, from the fermentation broth, the various avermectin compounds will be found to have been prepared in unequal amounts. In particular an "a" series compound will be prepared in a higher proportion that the corresponding "b" series compound. The weight ratio of "a" series to the corresponding "b" series is about 75:25 to 99:1. The differences between the "a" series and "b" series is constant throughout the avermectin compounds and consists of a sec-butyl group and an iso-propyl group respectively at the 25-position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular, for the preferred B1 and A1 compounds, it has been found that the starting materials for the compounds of this invention are very often prepared in a ratio of about 80% avermectin B1a and A1a and 20% avermectin B1b or A1b. Thus the preferred composition of this invention is one which contains at least 80% of the "a" component and not more than 20% of the "b" component.

EXAMPLE 1

Effects of Avermectin B1a/B1b and Agricultural Spray Oil on Cirtus Rust Mite on Oranges In a test of the effectiveness of avermectin compounds and agricultural spray oil (Sunspray 6N) used alone and in combination against the citrus rust mite on Marrs oranges, the following results were observed after spraying the orange trees to runoff with the listed concentration of the ingredients.

The data are given in Table I in terms of the mean numbers of rust mites observed per sq cm on the indicated number of days following the spraying. The agricultural spray oil was reapplied on day 53. The last column "% Russet" indicates the percent of fruit that were downgraded due to the effects of the mites.

TABLE I

| Treatment | oz./100 gal | Mean No. rust mite/sq. cm. (on fruit) | | | | | | | % Russet |
| --- | --- | --- | --- | --- | --- | --- | --- | --- | --- |
| | | Pretreatment | day 13 | day 26 | day 52 | day 67 | day 77 | day 96 | |
| Avermectin B1a/B1b | 0.04 | 1.52 | 0.00 | 0.00 | 0.14 | 4.56 | 5.78 | 15.13 | 35 |
| Avermectin B1a/B1b | 0.08 | 0.32 | 0.00 | 0.01 | 0.88 | 2.43 | 3.47 | 3.78 | 16 |
| Avermectin B1a/B1b & Agricultural Spray Oil | 0.04+ 0.25% | 0.30 | 0.04 | 0.00 | 0.06 | 0.50 | 0.00 | 0.24 | 5 |
| Agricultural Spray Oil | 0.25% | 0.72 | 0.00 | 0.01 | 1.62 | 1.57 | 1.35 | 0.78 | 31 |
| Control | — | 0.68 | 10.41 | 19.85 | 51.88 | 24.58 | 23.05 | 5.31 | 51 |

EXAMPLE 2

Effects of Avermectin B1a/B1b and Agriculture Spray Oil on Citrus Rust Mite on Grapefruit The procedure followed in Example 1 is repeated on grapefruit trees except that both the 0.04 oz/100 gal treatment of avermectin and the agricultural spray oil were reapplied on day 53. The results are given in Table II.

TABLE II

| Treatment | oz./100 gal | Mean No. rust mite/sq. cm. (on fruit) | | | | | | | % Russet |
| --- | --- | --- | --- | --- | --- | --- | --- | --- | --- |
| | | Pretreatment | day 13 | day 26 | day 52 | day 67 | day 77 | day 96 | |
| Avermectin B1a/B1b | 0.04 | 7.84 | 4.31 | 4.97 | 12.85 | 0.01 | 2.03 | 1.35 | 23 |
| Avermectin B1a/B1b | 0.08 | 4.36 | 0.19 | 0.15 | 3.48 | 1.42 | 1.22 | 1.55 | 22 |

TABLE II-continued

| Treatment | oz./100 gal | Mean No. rust mite/sq. cm. (on fruit) | | | | | | | % Russet |
|---|---|---|---|---|---|---|---|---|---|
| | | Pretreatment | day 13 | day 26 | day 52 | day 67 | day 77 | day 96 | |
| Avermectin B1a/B1b & Agricultural Spray Oil | 0.04 + 0.25% | 3.08 | 0.10 | 0.61 | 1.28 | 0.62 | 0.02 | 0.01 | 8 |
| Agricultural Spray Oil | 0.25% | 1.92 | 8.72 | 14.39 | 30.34 | 0.76 | 1.90 | 1.35 | 40 |
| Control | — | 9.28 | 55.05 | 30.24 | 11.68 | 2.00 | .47 | 0.13 | 70 |

In analyzing the result of Examples 1 and 2 it is noted that the 2 concentrations of the avermectin applied without oil achieved only moderate control of the mitts although the lower dosage in the grapefruit had to be reapplied because of increasing mite population levels. The agricultural spray oil, also applied twice, achieved a level of control better than the control group, but not very effective considering the high percent of russet downgrading of the fruit. The combination of a low dose of the avermectin and the agricultural spray oil applied once achieved in the orange test a mite count 60 times better than the low dose and 15 times better than higher dose at the end of the test. Percent russet was only 5% for the combination and 16 and 35% for the high and low doses respectively, 31% for the oil alone and 51% for the control. For the grapefruit, compared with the avermectin results, the combination had 135 and 155 times less mites. The percent russet was likewise improved at 8% for the combination 22 and 23% for avermectin alone, 40% for the oil alone and 70% for the control.

EXAMPLE 3

Effects of Avermectin and Agricultural Spray Oil Against Motile Stages of the Two-Spotted Spider Mite on Bean Plants in the Laboratory In this test various concentrations of avermectin B1a/B1b alone and in combination with two different levels of agricultural spray oil were tested. In addition, the agricultural spray oil alone was tested at 2 different concentrations. Table III shows the results where avermectin B1a/B1b was sprayed onto the plants containing a mixed mite population of adults and nymphs. Mortality counts were taken 5 and 11 days post-spray. Table IV represents a similar test however the infestation was applied 7 days after the plant was sprayed to measure residual control. Table V is a compilation of the data of Tables III and IV and gives the estimated effective dosage for avermectin B1a/B1b alone and with the agricultural spray oil.

TABLE III

Contact miticidal efficacy of Avermectin B1a/B1b Agricultural Spray Oil combinations

| | RATE (ppm) | 5-DAYS POST-SPRAY | | | | | |
|---|---|---|---|---|---|---|---|
| | | ADULTS | | | NYMPHS | | |
| TREATMENT | Avermectin B1a/B1b | Dead | Alive | % Cont. | Dead | Alive | % Cont. |
| Avermectin B1a/B1b | .25 | 131 | 0 | 100 | 9 | 0 | 100 |
| | .125 | 83 | 2 | 98 | 23 | 1 | 96 |
| | .063 | 126 | 32 | 80 | 23 | 0 | 100 |
| | .031 | 66 | 16 | 81 | 11 | 0 | 100 |
| | .015 | 56 | 40 | 58 | 3 | 0 | 100 |
| Avermectin B1a/B1b with 0.125% Agricul. Spray Oil | .1 | 138 | 0 | 100 | 8 | 0 | 100 |
| | .05 | 79 | 0 | 100 | 10 | 0 | 100 |
| | .025 | 175 | 0 | 100 | 9 | 0 | 100 |
| | .0125 | 160 | 0 | 100 | 10 | 0 | 100 |
| | .0063 | 124 | 1 | 99 | 11 | 0 | 100 |
| Avermectin B1a/B1b with 0.031% Agricul. Spray Oil | .1 | 125 | 1 | 99 | 19 | 0 | 100 |
| | .05 | 223 | 0 | 100 | 17 | 1 | 95 |
| | .025 | 196 | 0 | 100 | 9 | 0 | 100 |
| | .0125 | 139 | 0 | 100 | 15 | 0 | 100 |
| | .0063 | 216 | 4 | 98 | 9 | 4 | 69 |
| Controls: 0% | 0 | 0 | 162 | 0 | 0 | 6 | 0 |
| Agricul. .03% | 0 | 2 | 99 | 2 | 0 | 2 | 0 |
| Spray Oil .125% | 0 | 0 | 85 | 0 | 0 | 6 | 0 |

| | RATE (ppm) | 11 DAYS POST-SPRAY | | | | | | | |
|---|---|---|---|---|---|---|---|---|---|
| | | ADULTS | | | NYMPHS | | | LARVE | | |
| TREATMENT | Avermectin B1a/B1b | Dead | Alive | % Cont. | Dead | Alive | % Cont. | Dead | Alive | % Cont. |
| Avermectin B1a/B1b | .25 | 56 | 109 | 34 | 89 | 0 | 100 | 2 | 1 | 67 |
| | .125 | 51 | 131 | 28 | 55 | | 97 | 6 | 0 | 100 |
| | .063 | NC | | 0 | NC | | 0 | NC | | 0 |
| | .031 | NC | | 0 | NC | | 0 | NC | | 0 |
| | .015 | NC | | 0 | NC | | 0 | NC | | 0 |
| Avermectin B1a/B1b with 0.125% Agricul. Spray Oil | .1 | 113 | 2 | 98 | 17 | 1 | 95 | 188 | 0 | 100 |
| | .05 | 75 | 0 | 100 | 26 | 0 | 100 | 100 | 0 | 100 |
| | .025 | 106 | 17 | 86 | 71 | 1 | 99 | 76 | 0 | 100 |
| | .0125 | 143 | 13 | 92 | 77 | 10 | 89 | 50 | 0 | 100 |
| | .0063 | 224 | 41 | 85 | 40 | 27 | 60 | 64 | 0 | 100 |
| Avermectin B1a/B1b with 0.031% Agricul. | .1 | 117 | 4 | 97 | 37 | 1 | 97 | 14 | 2 | 88 |
| | .05 | 174 | 1 | 100 | 50 | 2 | 96 | 6 | 0 | 100 |
| | .025 | 123 | 7 | 95 | 36 | 12 | 75 | 40 | 0 | 100 |

TABLE III-continued
Contact miticidal efficacy of Avermectin B1a/B1b Agricultural Spray Oil combinations

| | | | | | | | | | | |
|---|---|---|---|---|---|---|---|---|---|---|
| Spray Oil | .0125 | 111 | 46 | 71 | 15 | 47 | 24 | 0 | 0 | |
| | .0063 | 120 | 32 | 79 | 32 | 49 | 40 | 2 | 0 | 100 |
| Controls: 0% | 0 | 0 | 96 | 0 | 0 | 43 | 0 | 0 | 75 | 0 |
| Agricul. .03% | 0 | | NC | 0 | | NC | 0 | | NC | 0 |
| Spray Oil .125% | 0 | | NC | 0 | | NC | 0 | | NC | 0 |

NC = no control

TABLE IV
Residual miticidal efficacy of Avermectin B1a/B1b Agricultural Spray Oil combinations

4-DAYS POST-SPRAY (11 days post-spray)

| TREATMENT | RATE (ppm) Avecmectin B1a/B1b | ADULTS Dead | Alive | % Cont. | NYMPHS Dead | Alive | % Cont. |
|---|---|---|---|---|---|---|---|
| Avermectin | 2.0 | 140 | 0 | 100 | 16 | 0 | 100 |
| B1a/B1b | 1.0 | 76 | 2 | 98 | 9 | 1 | 90 |
| | .05 | 39 | 0 | 100 | 12 | 0 | 100 |
| | 0.25 | 55 | 4 | 93 | 2 | 2 | 50 |
| Avermectin | 0.125 | 193 | 0 | 100 | 25 | 0 | 100 |
| B1a/B1b | 0.063 | 86 | 4 | 96 | 35 | 0 | 100 |
| with 0.125% | 0.031 | 75 | 4 | 95 | 24 | 3 | 89 |
| Agricultural | 0.015 | 49 | 49 | 50 | 8 | 14 | 36 |
| Spray Oil | | | | | | | |
| Avermectin | 0.125 | 83 | 2 | 98 | 14 | 7 | 67 |
| B1a/B1b | 0.063 | 91 | 2 | 98 | 6 | 2 | 75 |
| with 0.031% | 0.031 | 58 | 11 | 84 | 10 | 18 | 36 |
| Agricultural | 0.015 | 17 | 26 | 40 | 5 | 16 | 24 |
| Spray Oil | | | | | | | |
| Controls: 0% | 0 | 4 | 77 | 5 | 0 | 4 | 0 |
| Agricul. .03% | 0 | 3 | 58 | 5 | 0 | 9 | 0 |
| Spray Oil .125% | 0 | 0 | 86 | 0 | 0 | 5 | 0 |

13 DAYS POST-SPRAY (20 days post-spray)

| TREATMENT | RATE (ppm) Avermectin B1a/B1b | ADULTS Dead | Alive | % Cont. | NYMPHS Dead | Alive | % Cont. | LARVE Dead | Alive | % Cont. |
|---|---|---|---|---|---|---|---|---|---|---|
| Avermectin | 2.0 | 60 | 0 | 100 | 11 | 0 | 100 | 4 | 0 | 100 |
| B1a/B1b | 1.0 | 51 | 0 | 100 | 12 | 0 | 100 | 6 | 0 | 100 |
| | 0.5 | 40 | 0 | 100 | 16 | 0 | 100 | 21 | 0 | 100 |
| | 0.25 | 13 | 163 | 7 | 2 | 36 | 5 | 1 | 4 | 20 |
| Avermectin | 0.125 | 60 | 0 | 100 | 19 | 0 | 100 | 7 | 0 | 100 |
| B1a/B1b | 0.063 | 43 | 0 | 100 | 21 | 0 | 100 | 7 | 0 | 100 |
| with 0.125% | 0.031 | 73 | 20 | 78 | 15 | 10 | 60 | 4 | 0 | 100 |
| Agricultural | 0.015 | 25 | 140 | 15 | 4 | 41 | 9 | 0 | 5 | 0 |
| Spray Oil | | | | | | | | | | |
| Avermectin | 0.125 | 43 33 | 57 | 13 | 13 | 50 | 0 | 0 | 0 | |
| B1a/B1b | 0.063 | 34 | 37 | 48 | 8 | 7 | 53 | 1 | 0 | 0 |
| with 0.031% | 0.031 | NC | | | NC | | 0 | NC | | 0 |
| Agricultural | 0.015 | NC | | 0 | NC | | 0 | NC | | 0 |
| Spray Oil | | | | | | | | | | |
| Controls: 0% | 0 | NC | | 0 | NC | | 0 | NC | | 0 |
| Agricul. .03% | 0 | NC | | 0 | NC | | 0 | NC | | 0 |
| Spray Oil .125% | 0 | NC | | 0 | NC | | 0 | NC | | 0 |

NC = no control

TABLE V
Estimated effective dosages of Avermectin B1a/B1b combinations.

| | ED90s | | | |
|---|---|---|---|---|
| | CONTACT TEST | | RESIDUAL TEST | |
| | 5 Days Post-Spray | 11 Days Post-Spray | 4 Days Post-Infestation | 13 Days Post-Infestation |
| ADULTS | | | | |
| Avermectin B1a/B1b | .1 | .25 | .25 | .4 |
| Avermectin B1a/B1a with .125% Agricultural Spray Oil | .0063 | .025 | .03 | .05 |
| Avermectin B1a/B1b with .031% Agricultural Spray Oil | .0063 | .02 | .03 | .125 |
| NYMPHS | | | | |
| Avermectin B1a/B1b | .015 | .1 | .4 | .2 |
| Avermectin B1a/B1b with .125% Agricuiltural Spray Oil | .0063 | .0125 | .031 | .125 |
| Avermectin B1a/B1b with .031% Agricultural Spray Oil | .01 | .04 | .125 | .125 |
| LARVAE | | | | |
| Avermectin B1a/B1b | — | .1 | — | .4 |
| Avermectin B1a/B1b with 125% Agricul- | — | .0063 | — | .02 |

TABLE V-continued
Estimated effective dosages of Avermectin B1a/B1b combinations.

| | ED$_{90}$s | | | |
|---|---|---|---|---|
| | CONTACT TEST | | RESIDUAL TEST | |
| | 5 Days Post-Spray | 11 Days Post-Spray | 4 Days Post-Infestation | 13 Days Post-Infestation |
| tural Spray Oil Avermectin B1a/B1b with .031% Agricultural Spray Oil | — | .0063 | — | .125 |

In the above tests it is noted that the combination treatment is more effective than either treatment alone such that lower concentrations of the avermectin are effective for longer periods of time. In addition, since in the avermectin and combination treated plants many mites are recovered, although most are dead, it is apparent that the effect is not as an ovicide which would be expected with treatment with an oil. The presence of motile mites demonstrates that the eggs were not killed. However, the high mortality observed against the adults, nymphs and larvae populations also demonstrates that the treatment is highly effective against the motile stages of the mite.

EXAMPLE 4

Effects of Avermectins and Agricultural Spray Oil on the Two-spotted Spider Mite on Bean Plants Bean plants were treated with various concentrations of avermectin B1a/B1b, Sunspray 6N agricultural spray oil, and combinations thereof, and 7 days thereafter were challenged with a mixed population of the two-spotted spider mite. Table VI gives the results of observations made 6 and 12 days after the challenge. A significant improvement in activity is noted when the combination is applied to the plant.

TABLE VI
EVALUATION OF AVERMECTIN B1a/B1b WITH AGRICULTURAL SPRAY OIL TWO-SPOTTED SPIDER MITE

| Avermectin B1a/B1b PPM | Sunspray 6N Oil % | % Mortality | | | | |
|---|---|---|---|---|---|---|
| | | 6 Day Reading | | 12 Day Reading | | |
| | | Adults | Larvae | Adults | Nymphs | Larvae |
| 1.0 | — | 99 | 0 | 100 | 41 | 95 |
| 0.25 | — | 0 | 0 | 36 | 1 | 3 |
| 0.063 | — | 0 | 0 | 0 | 0 | 0 |
| 1.0 | 1.0 | 100 | 66 | 100 | — | 100 |
| 0.25 | 1.0 | 100 | 21 | 100 | — | 100 |
| 0.063 | 1.0 | 100 | 0 | 100 | 67 | 95 |
| 1.0 | 0.25 | 100 | 57 | 100 | — | 100 |
| 0.25 | 0.25 | 100 | 0 | 100 | 100 | 100 |
| 0.063 | 0.25 | 100 | 0 | 100 | 81 | 95 |
| 1.0 | 0.063 | 100 | 57 | 100 | 100 | 100 |
| 0.25 | 0.063 | 100 | 0 | 100 | — | 100 |
| 0.063 | 0.063 | 88 | 0 | 100 | 45 | — |
| — | — | 7 | 0 | 0 | 0 | 0 |
| — | 1.0 | 0 | 0 | 0 | 0 | 0 |
| — | 0.25 | 15 | 0 | 0 | 0 | 0 |
| — | 0.063 | 0 | 0 | — | — | — |

Bean plants were challenged with mixed mite population seven days after treatment.

EXAMPLE 5

Effects of Avermectin B1a/B1b, and Agricultural Spray Oil on the Citrus Red Mite on Lemon Trees Lemon trees with an ongoing population of citrus red mites were sprayed once with 8 ppm of avermectin B1a/B1b, agricultural spray oil and a combination thereof. The agricultural spray oil was applied at a rate of 3 pints per 100 gallons of spray (0.375%). The data is summarized in Table VII.

TABLE VII
CITRUS RED MITE, *Panonychus citri* on Lemon plants.

| | No. Mites per 32 Leaves Days Before of After Spraying | | | | | |
|---|---|---|---|---|---|---|
| Material & Rate | −5 | +7 | +16 | +30 | +50 | +70 |
| Avermectin B1a/B1b, 8 ppm | 26.7 | 0 | 0.3 | 24.7 | 15.0 | 18.3 |
| Avermectin B1a/B1b, 8 ppm + Agricultural Spray Oil* | 33.3 | 0 | 0 | 3.0 | 1.3 | 2.7 |
| NR-415 Agricultural Spray Oil* | 35 | 0 | 1.6 | 11.3 | 15.7 | 36.7 |
| Water (control) | 11.3 | 11.7 | 31 | 81.7 | 58.3 | 26.7 |

*3 pints per 100 gallons (0.375%)

EXAMPLE 6

Effects of Avermectins and Agricultural Spray Oils on Bean Aphids

Bean plants infested with the Bean aphids were treated with avermectin B1a/B1b, agricultural spray oil and mixtures thereof and the results analyzed 1 and 5 days after treatment. The results are summarized in Tables VIII and IX, and demonstrate that the oil has very little effect alone, and together the treatment is greatly and synergistically improved.

TABLE VIII
THE EFFECT OF AGRICULTURAL SPRAY OIL ON THE INSECTICIDAL EFFICACY OF AVERMECTIN B1a/B1b Bean Aphid on Bean Plants

| % Emulsifiable Oil | Concentration (PPM) of avermectin B1a/B1b | % Mortality[1] | |
|---|---|---|---|
| | | Day 1 | Day 5 |
| .25 | .5 | 0 | 90 |
| | .25 | 5 | 80 |
| | .125 | 0 | 85 |
| | .063 | 0 | 80 |
| | 0 | 0 | 5 |
| .063 | .5 | 25 | 50 |
| | .25 | 30 | 50 |
| | .125 | 10 | 60 |
| | .063 | 15 | 55 |
| | 0 | 5 | 0 |
| 0 | 1.0 | 30 | 35 |
| | 0.5 | 20 | 25 |
| | 0.25 | 25 | 0 |
| | 0.125 | 10 | 0 |
| | 0 | 0 | 0 |

[1] All values are means of 2 replicates

TABLE IX
Influence of an agricultural spray oil on the efficacy of avermectin B1a/B1b used against the bean aphid

| Percent Oil | avermectin B1a/B1b (ppm) | Percent Control[a] |
|---|---|---|
| 0.25 | 0.5 | 87 |
| | 0.125 | 53 |
| | 0.031 | 17 |
| | 0.0078 | 0 |
| | 0 | 0 |
| 0.125 | 0.5 | 80 |
| | 0.125 | 33 |
| | 0.031 | 0 |
| | 0.0078 | 0 |
| | 0 | 0 |
| 0.063 | 0.5 | 73 |
| | 0.125 | 30 |
| | 0.031 | 0 |
| | 0.0078 | 0 |

TABLE IX-continued

Influence of an agricultural spray oil on the efficacy of avermectin B1a/B1b used against the bean aphid

| Percent Oil | avermectin B1a/B1b (ppm) | Percent Control[a] |
|---|---|---|
|   | 0 | 0 |
| 0 | 0.5 | 47 |
|   | 0.125 | 3 |
|   | 0.031 | 0 |
|   | 0.0078 | 0 |
|   | 0 | 0 |

[a]Mean of three replicates

EXAMPLE 7

Preparation of an Aqueous Plant Spray Containing Avermectin B1a/B1b and an Agricultural Spray oil For evaluation of synergistic activity in the laboratory, a 90% oil emulsion was formulated by adding 1 gram of Agrimul 26-B emulsifier to 9 grams of Sunspray 6N 60 sec spray oil. This oil emulsion was treated as a pure (100%) oil and added to solutions of avermectin B1a/B1b to prepare known concentrations of the avermectins and oil as shown in the foregoing examples.

For dilute spray applications under field conditions, 0.04 oz of avermectin B1a/B1b formulated as 0.03 lb per gallon soluble liquid was poured into 100 gal of water. To this resulting solution was added with agitation 1 quart of agricultural spray oil to provide an emulsion containing 0.04 oz avermectin B1a/B1b (3 ppm) and 0.25% oil in 100 gal of water.

EXAMPLE 8

In greenhouse studies on twospotted spider mites (*Tetranychus urticae*) on bean leaves, the results show conclusively that avermectin B1a/B1b is significantly more effective and persistent as a miticide when compared with milbemycin B-41D (13-deoxy-22,23-dihydro avermectin B1b aglycone). In short term contact studies both avermectin B1a/B1b and milbemycin B-41D showed comparable potency. However, in long term residual studies showed that avermectin B1a/B1b was 32–64 times more active than milbemycin B-41D.

Even more significantly, the addition of an agricultural spray oil to avermectin B1a/B1b resulted in it being nearly 100 times more effective than the milbemycin B-41D. The addition of the agricultural spray oil to milbemycin B-41D actually resulted in a decrease in the residual activity.

The protocol for the tests is given below and the data are summarized in Table X.

Preparation of Test Solutions

A solution of Triton X-155 in acetone (1000 ppm) was used to dissolve the material under test and the resultant solution was diluted with water to obtain a mixture of 10% acetone and 100 ppm of Triton X-155 in water. Further dilution of this stock solution as required in a test was done by using Triton X-155 at 100 ppm in water so that a constant ratio of the surfactant was maintained at all levels. Where emulsifiable oil was used in the treatments, the solutions were prepared in such a way that the final solutions contained 0.06% v/v of the oil.

Plants and Mites

Leaves of Sieva bean plants grown from seeds planted 14–21 days earlier were used in all the tests. Twospotted spider mites (*Tetranychus urticae*) were cultured continuously on sieva bean plants growing in an insectary under continuous lighting at 75° F.

Procedure for Studying Contact Activity

On day 0, eight leaves which had been infested with mites 24 hours earlier were dipped in the treatment solution. On Day 5, mortality was assessed on four of the leaves and on Day 12 on the remaining four leaves.

Procedure for Studying Residual Activity

On Day 0, eight uninfested leaves were treated by immersion in the treatment solution. On Day 7, all the leaves were infested with a mixed population of mites. On Day 13, mortality was assessed on four of the leaves and on Day 19 on the remaining four leaves.

TABLE X

Avermectin B1a/B1b and Milbemycin B-41D - Contact and Residual Activity on Bean Leaves Against the 2-Spotted Spider Mites (*Tetranychus urticae*)
A = Adults, N = Nymphs, L = Larvae

1. CONTACT ACTIVITY*#

| | 0.06 ppm | | | 0.015 ppm | | | 0.004 ppm | | | 0.001 ppm | | |
|---|---|---|---|---|---|---|---|---|---|---|---|---|
| | A | N | L | A | N | L | A | N | L | A | N | L |
| Milbemycin B-41D + oil | | | | | | | | | | | | |
| 5-Day | 84 | — | — | 30 | — | — | 17 | — | — | 39 | — | — |
| 12-Day | 38 | 59 | 95 | 34 | 22 | 46 | NC | NC | NC | NC | NC | NC |
| Avermectin B1a/B1b + oil | | | | | | | | | | | | |
| 5-Day | 99 | — | — | 98 | — | — | 28 | — | — | NC | NC | NC |
| | | | | | | | | very few eggs present | | | | |
| 12-Day | 96 | 100 | 100 | 83 | 100 | 100 | NC | NC | NC | NC | NC | NC |

| | 0.25 ppm | | 0.06 ppm | | | 0.015 ppm | | | 0.04 ppm | | |
|---|---|---|---|---|---|---|---|---|---|---|---|
| | A | L | L | A | N | L | A | N | L | A | N | L |
| Milbemycin B-41D only | | | | | | | | | | | | |
| 5-Day | 100 | — | — | 92 | — | — | 66 | — | — | 79 | — | — |
| 12-Day | 43 | 67 | 100 | 38 | 56 | 91 | NC | NC | NC | NC | NC | NC |
| Avermectin B1a/B1b only | | | | | | | | | | | | |

TABLE X-continued

Avermectin B1a/B1b and Milbemycin B-41D -
Contact and Residual Activity on Bean Leaves Against
the 2-Spotted Spider Mites (*Tetranychus urticae*)
A = Adults, N = Nymphs, L = Larvae

| | | | | | | | | | | | | |
|---|---|---|---|---|---|---|---|---|---|---|---|---|
| 5-Day | 100 | — | — | 99 | — | — | 48 | — | — | NC | NC | NC |
| 12-Day | 86 | 88 | 100 | 37 | 94 | 82 | NC | NC | NC | NC | NC | NC |

2. RESIDUAL ACTIVITY##

| | 2.0 ppm | | | 0.5 ppm | | 0.125 ppm | | 0.03 ppm | |
|---|---|---|---|---|---|---|---|---|---|
| | A | N | L | A | N | A | N | A | N |
| Milbemycin B-41D + oil | | | | | | | | | |
| 6-Day | 17 | 8 | — | 5 | NC | NC | NC | NC | NC |
| 12-Day | 27 | 75 | 74 | NC | NC | NC | NC | NC | NC |

| | 0.5 ppm | | | 0.125 ppm | | | 0.031 ppm | | | 0.008 ppm | |
|---|---|---|---|---|---|---|---|---|---|---|---|
| | A | N | L | A | N | L | A | N | L | A | N |
| Avermectin B1a/B1b + oil | | | | | | | | | | | |
| 6-Day | 96 | 100 | — | 99 | 100 | — | 65 | 57 | — | 4 | NC |
| 12-Day | 100 | 100 | 100 | 100 | 100 | 100 | 26 | 4 | 23 | NC | NC |

| | 16 ppm | | | 4 ppm | | | 1 ppm | | | 0.25 ppm | | |
|---|---|---|---|---|---|---|---|---|---|---|---|---|
| | A | N | L | A | N | L | A | N | L | A | N | L |
| Milbemycin B-41D only | | | | | | | | | | | | |
| 6-Day | 50 | 57 | — | 6 | 0 | — | NC | NC | — | NC | NC | — |
| 12-Day | 88 | 78 | 100 | 15 | 2 | 53 | NC | NC | NC | NC | NC | NC |

| | 1.0 ppm | | | 0.5 ppm | | | 0.25 ppm | | | 0.125 ppm | | |
|---|---|---|---|---|---|---|---|---|---|---|---|---|
| | A | N | L | A | N | L | A | N | L | A | N | L |
| Avermectin B1a/B1b only | | | | | | | | | | | | |
| 6-Day | 100 | 100 | — | 100 | 78 | — | 15 | 0 | — | 34 | 0 | — |
| 12-Day | 100 | 100 | 100 | 100 | 100 | 100 | NC | NC | NC | NC | NC | NC |

*Figures given are names of four replicates.
Oil was used at 0.06% concentration in the treatment solution.
The leaves were infected 6 and 12 days after treatment.
The mites were treated on Day 0 and counted 5 and 12 days later.
NC = No control was seen.
— = None present.

Example 9

In the field experiments of citrus rust mites (*Phyllocoptruta oleivora*) on citrus it was shown that avermectin B1a/B1b with an agricultural spray oil is nearly 14 times more effective than milbemycin B-41D also in oil. The data further show that the addition of the oil to milbemycin B-41D decreased the efficacy thereof. The protocol is given below and the data are summarized in Table XI.

Application of Treatments

Citrus (pink grapefruit) trees (which were 5–7 years old) infested with citrus rust mites (*Phyllocoptrura oleivora*) were sprayed using a hydraulic handgun at 250 psi. Each tree was sprayed until runoff.

Evaluation

Each treatment consisted of three replicates. Thirty-three leaves from each tree were evaluated for percent leaf area not infested by mites. These evaluations were done before the application of treatments and 7 and 14 days after the application of treatments.

TABLE XI

Efficacy of Avermectin B1a/B1b and
Milbemycin B-41D Formulations on Citrus Rust Mite
(*Phyllocoptruta oleivora*) Infestation on Citrus in Florida.

| | | Percent control *days after treatment | |
|---|---|---|---|
| Treatment | Rate ai/100 gal | 7 | 14 |
| Avermectin B1a/B1b | 0.04 oz + 0.25% oil | 62 | 87 |
| Milbemycin B-41D | 0.04 oz + 0.25% oil | 4 | 6 |
| Milbemycin B-41D | 0.04 oz | 14 | 13 |
| Milbemycin B-41D | 0.2 oz | 16 | 18 |

*Mean of 100 leaves from 3 trees.

What is claimed is:

1. An aqueous synergistic composition for use against the motile stages of mites and insect pests of plants which comprises an inert carrier, a compound having the formula:

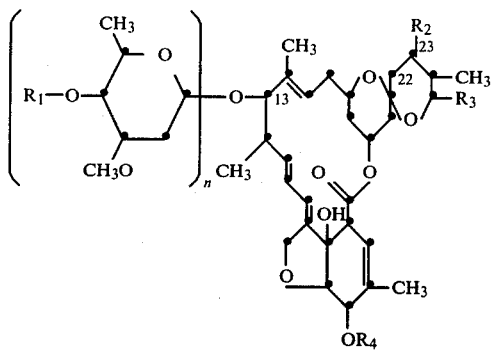

wherein
the broken line indicates either a single or a double bond at the 22,23-position;
n is 0 or 1 such that when n is 0 a hydroxy is present at the 13-position;
$R_1$ is hydrogen or

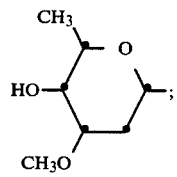

$R_2$ is hydrogen or hydroxy, provided that $R_2$ is present only when the broken line indicates a single bond;
$R_3$ is sec-butyl or isopropyl; and
$R_4$ is hydrogen or methyl,
and an agricultural spray oil consisting of a non-phytotoxic, highly refined hydrocarbon oil of at least 92% unsulfonated residues such that the active ingredient is present at from 0.03 to 8 ppm, and the agricultural spray oil is present at from 0.06 to 0.5%.

2. The synergistic composition of claim 1 wherein the avermectin compound or compounds is present at from 0.25 to 3 ppm and the agricultural spray oil is present at from 0.06 to 0.5% v/v.

3. The synergistic composition of claim 2 wherein the avermectin compound or compounds is present at from 1 to 3 ppm and the agricultural spray oil is present at about 0.25% v/v.

4. The composition of claim 1 which includes an anionic and/or a non-ionic surfactant.

5. A method for the treatment of the motile stages of arthropod pests of plants which comprises treating such plants with an aqueous synergistic combination of a compound having the formula:

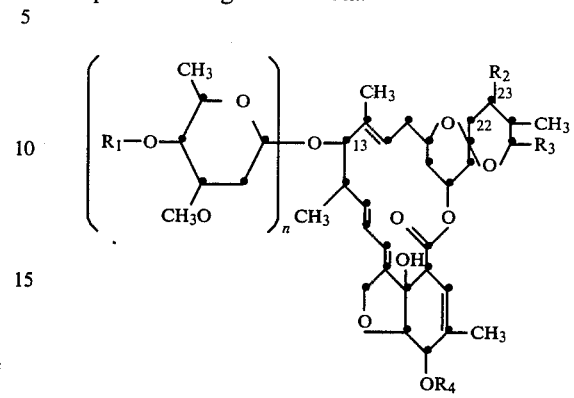

wherein
the broken line indicates either a single or a double bond at the 22,23-position;
n is 0 or 1 such that when n is 0 a hydroxy is present at the 13-position;
$R_1$ is hydrogen or

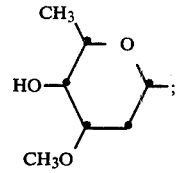

$R_2$ is hydrogen or hydroxy provided that $R_2$ is present only when the broken line indicates a single bond;
$R_3$ is sec-butyl or isopropyl; and
$R_4$ is hydrogen or methyl, and an agricultural spray oil consisting of a non-phytotoxic, highly refined hydrocarbon oil of at least 92% unsulfonated residues such that the active ingredient is present at from 0.03 to 8 ppm, and the agricultural spray oil is present at from 0.06 to 0.5%.

6. The method of claim 5 wherein the avermectin compound or compounds is present at from 0.25 to 3 ppm and the agricultural spray oil is present at from 0.06 to 0.5% v/v.

7. The method of claim 6 wherein the avermectin compound or compounds is present at from 1 to 3 ppm and the agricultural spray oil is present at about 0.25% v/v.

* * * * *